United States Patent [19]

Sydiskis et al.

[11] Patent Number: 4,670,265
[45] Date of Patent: Jun. 2, 1987

[54] ALOE EMODIN AND OTHER ANTHRAQUINONES AND ANTHRAQUINONE-LIKE COMPOUNDS FROM PLANTS VIRUCIDAL AGAINST HERPES SIMPLEX VIRUSES

[76] Inventors: Robert J. Sydiskis, 607 Southwarke Rd., Bel Air, Md. 21014; David G. Owen, 402 Hollen Rd., Baltimore, Md. 21212

[21] Appl. No.: 674,677

[22] Filed: Nov. 26, 1984

Related U.S. Application Data

[63] Continuation-in-part of Ser. No. 516,328, Jul. 22, 1983, abandoned.

[51] Int. Cl.$^4$ ..................... A61K 35/78; A61K 31/12
[52] U.S. Cl. ................................ 424/195.1; 514/680; 514/934
[58] Field of Search ..................... 424/195.1; 514/680, 514/934

[56] References Cited

U.S. PATENT DOCUMENTS 3,627,791 12/1971 Grisar et al. ..................... 260/371

OTHER PUBLICATIONS

The Merck Index, 9th ed., No. 3512, p. 3509, 1976.
Chem. Abstracts, 88:37503, 1978; 97:182023t, 1982; 82:91y, 1975; 87: 57282, 1977; 82: 106176v, 1975; 76:85650n, 1972.

Primary Examiner—Donald B. Moyer
Assistant Examiner—John W. Rollins, Jr.
Attorney, Agent, or Firm—Cushman, Darby & Cushman

[57] ABSTRACT

A method has been disclosed for treating type 1 or 2 herpes simplex virus comprising the successive steps of:
 (1) topically applying to the virus-affected areas of a person suffering from said virus, a topically effective amount of an anthaquinone, containing extract having an antiviral effect of type 1 or type 2 herpes simplex virus, and
 (2) repeating said topical application as required until the desired antiviral effect is observed.

8 Claims, 1 Drawing Figure

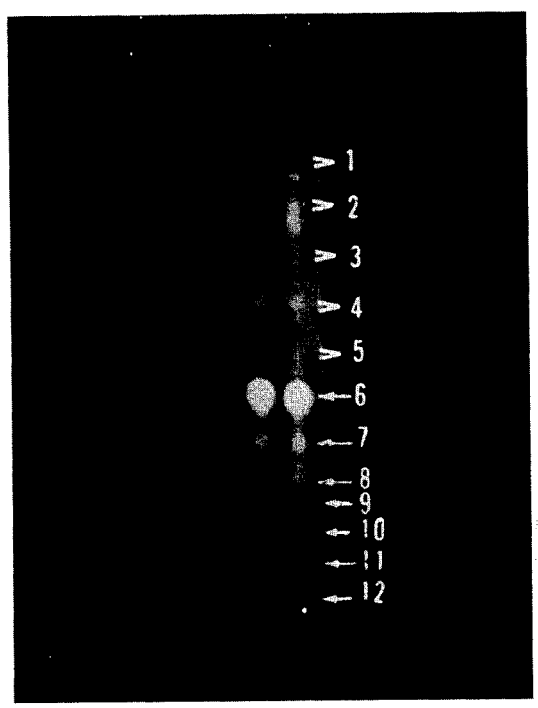

ALOE EMODIN AND OTHER ANTHRAQUINONES AND ANTHRAQUINONE-LIKE COMPOUNDS FROM PLANTS VIRUCIDAL AGAINST HERPES SIMPLEX VIRUSES

CROSS-REFERENCE TO RELATED APPLICATIONS

This application is a continuation-in-part of our earlier application Ser. No. 516,328 filed July 22, 1983, now abandoned.

FIELD OF THE INVENTION

This invention relates to the treatment of herpes simplex virus, types 1 and 2, with plant extracts containing Anthraquinones and Anthraquinone-like compounds.

BACKGROUND OF THE INVENTION

The use of plant exudates and gels from the Aloe vera plant is described extensively in the medical, folk and patent literature. Over the centuries, plants have served as the major source of medicines for mankinds treatment of disease. In fact it has only been in relatively recent times that synthesis and drug design have served to provide the drugs used in therapeutics. Never-the-less plants still have a part in folk and propriety medicine. These uses, in many instances, may be at variance with the use predicated by the type of activity afforded by the major phytoconstituent present. A large group of plants contain anthraquinones and anthraquinone-glycosides and because of this have been, and still are, used as laxatives.

Aloe vera is a prime example. It has been used for centuries as a source of Aloin and for its use as a laxative. However the leaves have also served as a source of gel which has had a wide and varied use. Aloe vera gel is the yellowish, viscous, watery gel secreted from the leaves of the Aloe vera plant and the gel has been reported to be used by primitive civilizations for the treatment of burns, kidney and bladder infections, prostatitis, dysentery and following periodontal surgery; R. Henry, An Updated Review of Aloe Vera, Cosmetics & Toiletries, Vol. 94, pp. 42–50 (1979). Topical wounds and burns are treated with a gel containing a salt of naturally occurring polyuronide derived from aloe in U.S. Pat. No. 3,013,466 to Farkas while a polysaccharide product derived from the juice of the aloe plant used for the treatment of wounds is described in Farkas' later patent 3,362,951. Aloe vera gel is described for the treatment of wounds, blisters and other lesions in U.S. Pat. Nos. 3,892,853 to Cobble and 3,360,511 to Maret. The effectiveness of Aloe vera in the treatment of thermal and radiation burns, wounds, chapped and dry skin, peptic ulcers, chronic ulcers and dermatoses is reported as are folk uses of Aloe vera for the treatment of venerial sores, boils, hemorrhoids and a host of other ailments; see A. Y. Leung, Aloe Vera in Cosmetics, D&CI, pp.34 (June 1977) and G. Gjerstad et al, Current Status of Aloe as a Cure-All, American Journal of Pharmacy, pp. 59–64 (March-April, 1968). However most other anthraquinone containing plants, except for those such as madder root (Rubia tinctorum) which are used as dyes, have been used for their laxative abilities.

DETAILED DESCRIPTION OF THE INVENTION

We have discovered that extracts prepared from the gel, sap or leaves of Aloe vera the bark of Frangula (Rhamnus frangula) and Cascara Sagrada (Rhamnus purshiana), the leaves of Senna (Cassia angustifolia), and the rhizome of Rhubarb (Rheum rhaponticum) have a marked anti-viral effect in vitro against both herpes simplex virus (HSV) type 1 and 2. It has also been shown to be effect in vivo in humans. The phytoconstituent responsible for this activity resides in a compound that has structural elements of the most common anthraquinones (perhaps a substituted dihydronaphthacene). The active compound can be extracted by, and partially purified with, a variety of solvents including acetone, ethyl acetate, methanol, and glycerin. The active compound can be resolved from non-active compounds in a methanol homogenate by Thin Layer Chromatography (TLC). At least twelve distinct zones can be visualized under ultraviolet light, removed and tested for their anti-viral acitivity by this method. The activity is located in a single zone on the top of the plate, which runs with the solvent front.

We have also discovered that, although the compound can be extracted with the above solvents, the best method of extraction to date is a hot glycerin extraction of the dried plant material. The active compound can be readily resolved and identified from these extracts on silica gel TLC plates run with a toluene/10% methanol solvent using purified aloe emodin as a marker.

The extract has a direct virucidal effect on HSV under the standardly accepted assay conditions employed. This effect is demonstrable by mixing the test extract directly with HSV and incubating the mixture for 15 minutes at 37° C., then diluting the mixture and assaying for the amount of viable HSV capable of producing plaques in an in vitro cell culture system. A plaque is defined as a visible, localized destruction of cells in culture produced by a single infectious virus particle or plaque forming unit and is the most sensitive assay in virology for quantitating viruses. Depending on the type and concentration of the test extract used, complete inactivation of HSV plaque forming units can be achieved in 15 minutes or less.

The compound responsible for this anti-viral activity could prove to be an effective anti-herpes drug with certain advantages over existing anti-herpes drugs. Its most obvious advantage is that it is non-toxic, at least at the activity levels present in the plants, since the gel, leaf and root extracts from the plants have been used extensively in a wide variety of cosmetic and "health food" products and ingested for many years without reported ill effects. Other available anti-herpes drugs are made analogs with toxic properties which require prescription use only In contrast, the compound reported herein has a well demonstrated lack of toxicity. Pharmaceutical presentations may include an ointment base for treating both recurrent cold sores, genital infections, and traumatic herpes infections; a mouthrinse for intraoral primary and recurrent infections; drops for treating primary and recurrent herpetic keratoconjunctivitis; and a douche for preventing and treating primary and recurrent vaginal infections. The extract may also be incorporated into disinfectants, sterilizing solutions and soaps as an anti-herpes agent. In addition, the extract may prove useful to veterinarians treating herpetic infections of animals.

ASSAY PROCEDURES

Material for testing was obtained from Aloe plants using either whole leaf homogenates, sap or gel. Other materials for testing included dried leaves of Aloe vera and Senna, dried bark of Frangula and Cascara, dried rhizomes of Rhubarb and a commercial preparation of Aloin. All samples were tested for anti-viral activity by a Plaque Reduction Assay (PRA) using monolayer cultures of Vero (African Green Monkey Kidney) cells grown in MEM+5% calf serum. The PRA procedure has been used routinely to assay anti-viral drugs; see Schwobel, Streissle and Kiefer, Adv. Ophthal, vol. 38, p. 38, (1979); Ebbesen, et al., Microbiologica vol. 2, p. 1919 (1979) and Rosenthal et al., Antimicrob. Agents and Chemo. vol 22, p. 1031 (1982). The PRA was performed by making serial ten-fold dilutions of the test samples in Eagle's Minimum Essential medium (MEM) containing penicillin, streptomycin and Fungizone. This medium also contains phenol red pH indicator. Therefore, any sample with an acid or alkaline pH could be easily titrated back to neutrality prior to addition of the pH-sensitive HSV. HSV stock samples were diluted to give a final starting concentration of approximately $10^5$ Plaque Forming Units (PFU) per 0.1 ml. A 0.1 ml volume of this HSV concentration was inoculated into each test sample dilution and placed in a 37° C. water bath for 15 minutes. Control samples contained 1 ml MEM or 50% Glycerin:water+0.1 ml of HSV. All samples were then diluted in phosphate buffered saline (PBS) to give a final HSV concentration of approximately 100 PFU/ml in the control samples. Samples were titrated for the number of PFU by inoculation of 1 ml of the appropriate dilution onto duplicate Vero cell monolayers in 60 mm dishes. After adsorption, the inoculum was removed, a methyl cellulose/MEM overlay medium was added and after three days incubation the number of plaques per dish counted and averaged. Each plaque formed was the result of infection of the cells by a single virus particle or PFU. The results were normalized between each experiment by setting the number of plaques obtained in the 15 minute control HSV dishes at 100% and calculating the average reduction of plaques in the test dishes as a percent of the control. Thus, all the PRA results reported here are presented as two numbers, for example $10^{-2}$ (100%). The first number represents the dilution of the test sample used in the PRA and the second number, in parentheses, represents the percent reduction in the average number of HSV PFU as compared with the control, a 100% value representing a complete reduction in PFU and a (0%) value representing no anti-viral activity, that is, no difference in PFU as compared with the control. Test samples dissolved in ethanol were assayed by the PRA at starting dilutions of $10^{-2}$. This was necessary since controls containing ethanol tested at $10^{-1}$ resulted in some reduction in PFU. Controls containing ethanol dilutions of $10^{-2}$ or greater gave no reduction in PFU as compared with normal aqueous (MEM) controls. The reproducibility of this PRA was tested and shown to plus-or-minus 10% or less. Except where noted in Examples 4 and 11, all PRA's used HSV-1 (KOS strain) only.

The invention will be more readily understood from a consideration of the following specific examples which are given for the purpose of illustration only and are by no means limiting or exhaustive.

EXAMPLE 1

Five ml of gel were obtained from an Aloe leaf by mechanically removing the epidermal layers of the leaf and harvesting the gel. The gel was diluted in MEM and tested for anti-viral activity by the PRA. The results were $2\times10^{-1}$ (100%) and $2\times10^{-2}$ (91%) indicating the Aloe gels contained anti-viral activity.

EXAMPLE 2

Three ml of sap were collected by allowing the sap to run from a freshly cut Aloe leaf, diluted in MEM and tested for anti-viral activity by the PRA. The results were $10^{-2}$ (100%), $10^{-3}$ (89%) and $10^{-4}$ (19%) showing that Aloe sap also contained anti-viral activity.

EXAMPLE 3

An Aloe plant leaf weighing 14.3 g was homogenized in 200 ml of ethyl acetate in a Waring blender. The homogenate was filtered through a #1 Watman filter, the filtrate collected and reduced to dryness in vacuo at 30° C. The dried filtrate was dissolved in 50 ml of ethyl acetate, filtered and again evaporated to dryness in vacuo. This residue was dissolved in 2 ml of 95% ethanol and tested for anti-viral activity by the PRA. The results were $10^{-2}$ (100%), $10^{-3}$ (61%). These results indicated that an ethyl acetate homogenate from whole leaves contained anti-viral activity.

EXAMPLE 4

The anti-viral activity present in methanol homogenates of whole leaves was active against both HSV-1 and HSV-2. A sample from a methanol homogenate of whole Aloe leaves (see example 5) was diluted $10^{-2}$ and $10^{-3}$ and tested by the PRA for anti-viral activity against both HSV-1 and HSV-2. The results were: HSV-1, $10^{-2}$ (100%), HSV-1, $10^{-3}$ (100%), HSV-2, $10^{-2}$ (100%), HSV-2, $10^{-3}$ (100%).

EXAMPLE 5

Leaves totaling 133 g were removed from an Aloe plant and homogenized in 300 ml of methanol. The homogenate was filtered, evaporated to dryness in vacuo, and the residue was suspended in 30 ml of methanol. Two ml of the methanol sample (sample A) were removed for testing by the PRA, the remainder was again evaporated to dryness in vacuo. The resulting material was washed three times with 50 ml ethyl acetate and the ethyl acetate washes pooled. Remaining residue was then washed three times with 50 ml of ethanol and the ethanol washed pooled. The pooled ethyl acetate (sample B) and ethanol washes (sample C) were flash evaporated separately and resuspended in 1.5 ml ethanol and tested by the PRA. The results were: Sample A: $10^{-3}$ (100%), $10^{-4}$ (22%); Sample B: $10^{-3}$ (100%), $10^{-4}$ (19%); Sample C: $10^{-3}$ (100%), $10^{-4}$ (100%), $10^{-5}$ (11%). These results show that the active compound from whole Aloe leaves could be partially purified and recovered in a greater concentration from the methanol homogenate by using ethanol as the extracting solvent rather than ethyl acetate.

EXAMPLE 6

A methanol extract was prepared by homogenizing 72.3 g of Aloe leaves in 300 ml methanol as in example 5. The residue resulting from the evaporation of this solvent was dissolved in acetone, evaporated in vacuo, redissolved in 1.5 ml ethanol and tested by the PRA. The results were $10^{-2}$ (100%), $10^{-3}$ (99%), and $10^{-4}$ (53%). These results demonstrated that although acetone can be also used as an extracting solvent, it results in less concentration of the activity than ethanol as shown in Example 5.

EXAMPLE 7

Eight, 5 microliter portions of sample A (methanol fraction from example 5) were spotted onto a polyamide (nylon) TLC plate and chromatographed against Egger's solvent consisting of chloroform: methylethyl ketone: methanol (3:2:1). Twelve zones were removed from six of the lanes by scraping. They were pooled, washed in ethyl acetate, filtered, evaporated in vacuo and dissolved in 1.5 ml ethanol for testing by the PRA at a $10^{-2}$ dilution. A blank control was prepared by scraping an unused portion of the developed plate. The remaining two lanes were photographed under ultraviolet light and the results can be seen in FIG. 1.

The results of the PRA assay reading from the top zone to the origin as 1 through 12 were: $1-10^{-2}$ (83%), $2-10^{-2}$ (4%), $3-10^{-2}$ (5%), $4-10^{-2}$ (3%), $5-10^{-2}$ (1%), $6-10^{-2}$ (5%), $7-10^{-2}$ (0%), $8-10^{-2}$ (0%), $9-10^{-2}$ (15%), $10-10^{-2}$ (0%), $11-10^{-2}$ (2%) and $12-1^{-2}$ (6%). The TLC control plate was $10^{-2}$ (9%). Of the twelve zones removed and tested, significant activity was recovered in only one zone (zone 1). The TLC plate is shown in FIG. 1.

BRIEF DESCRIPTION OF THE DRAWING

FIG. 1 is a representation of a thin layer chromatography plate of a methanol homogenate of whole Aloe vera leaves showing 12 distinct zones when viewed under ultra violet light, antiviral activity being located in a single zone at the top of the plate, which runs with the solvent.

EXAMPLE 8

The role of the variables of dose, time and temperature on the anti-viral effect was determined as follows. A portion of sample A (methanol fraction from example 5) was diluted to $10^{-2}$ and $10^{-3}$ and HSV added according to the PRA assay with the following modifications. Control and test samples were prepared at time zero by mixing and immediately diluting the samples, or prepared and incubated for either 5 minutes, 15 minutes, or 60 minutes and diluted. Samples were incubated at the indicated times at 4° C. and at 37° C. The results are summarized in the following table.

TABLE 1

| Time (min) | Temp. | Extract Dilution $10^{-2}$ | $10^{-3}$ |
| --- | --- | --- | --- |
| 0 | 4° C. | 0* | 0 |
| 5 | 4° C. | 46 | 0 |
| 15 | 4° C. | 54 | 0 |
| 60 | 4° C. | 91 | 22 |
| 0 | 37° C. | 8 | 5 |
| 5 | 37° C. | 95 | 19 |
| 15 | 37° C. | 100 | 99 |

*% activity (PRA assay)

These results demonstrated that the anti-viral activity was dependent on the time of incubation, temperature of incubation and the concentration of sample A.

EXAMPLE 9

The extent of virus inactivation was tested as follows. A portion of sample B (example 5) was evaporated in vacuo and the residue resuspended in water and labeled sample D. A PRA on sample D gave the following activity: $10^{-2}$ (100%). A portion of sample D was diluted 1:10 in MEM and mixed with $2.8 \times 10^5$ PFU of HSV, incubated for 15 minutes at 37° C. and the entire mixture added directly to a dish (dish 1) containing a monolayer of Vero cells. The virus was allowed to adsorb for 1.5 hours and the inoculum was removed and replaced with MEM+1% calf serum. A control for dish 1 without sample D was also prepared (dish 2), as well as cell cytotoxicity controls (dishes 3 and 4) as listed below.

TABLE 2

| | | Results | |
| --- | --- | --- | --- |
| Dish | Treatment | CPE* | Cytotoxicity** |
| 1 | Sample D $10^{-1}$ + $2.8 \times 10^5$ PFU | 0 | |
| 2 | MEM + $2.8 \times 10^5$ PFU | 4+ | |
| 3 | Sample D $10^{-1}$ + MEM | | 0 |
| 4 | MEM only | | 0 |

*CPE scale; 0 = CPE; 4+ = 100% CPE
**Cell cytotoxicity; 0 to 4+ scale. 0 = no effect on cell morphology to 4+ = gross changes in cell morphology By the third day of incubation, the control dish (dish 2) demonstrated a complete cytopathic effect (CPE) caused by HSV. However, in dish 1 no CPE was noted nor was any cytotoxicity effect of sample D noted on the cells (dish 3 vs. dish 4). Additional incubation of dishes 2, 3 and 4 for an additional 24 hours produced no changes in the cells.

Because no overlay medium was added to the infected Vero cells, a single infectious virus particle (PFU) infecting one cell in the dish would have eventually led to a complete destruction (CPE) of the entire cell monolayer. Since no evidence of any CPE could be detected in dish 1, these results demonstrated that the anti-viral activity in sample D effectively inactivated all $2.8 \times 10^5$ PFU used in this assay, a 5 log reduction in infectious virus particles.

EXAMPLE 10

This example demonstrated that: (1) the active compound can also be extracted using glycerin, and (2) an active compound is also present in other plants naturally rich in anthroquinone-like compounds. To extract with glycerin, 0.3 g of whole dried plant materials were mixed with 3 ml of glycerin at 105° C. for 20 min and the extract immediately filtered hot. The extract was then diluted to a final starting concentration of 1 mg/ml in 50% glycerin for assay by a PRA since it was found that 100% glycerin inactivates HSV in the controls. The results are listed in Table 3 below.

TABLE 3

| | Dilution | | | | |
| --- | --- | --- | --- | --- | --- |
| Plant Source | $10^{-2}$* | $10^{-3}$ | $10^{-4}$ | $10^{-5}$ | $10^{-6}$ |
| Aloe vera (dried leaf) | 100** | 100 | 45 | — | — |
| Frangula (dried bark) | 100 | 100 | 1 | 28 | — |
| Rhubarb (dried rhizome) | 100 | 100 | 100 | 100 | 93 |
| Cascara (dried bark) | 100 | 100 | 98 | 35 | — |
| Senna | 100 | 100 | 46 | — | — |

TABLE 3-continued

| Plant Source | Dilution | | | | |
|---|---|---|---|---|---|
| | $10^{-2}$* | $10^{-3}$ | $10^{-4}$ | $10^{-5}$ | $10^{-6}$ |
| (dried leaf) Control (50% glycerol) | 0 | 0 | 0 | 0 | 0 |

*starting concentration at $10^{-2}$ dilution = 1 mg/ml in 50% glycerol
**% activity (PRA assay)

EXAMPLE 11

The anti-viral activity present in hot glycerin extracts of plants was active against both HSV-1 and HSV-2. Dilutions of glycerin extracts from plants (from example 10) which gave 100% activity against HSV-1 in example 10 were retested by a PRA against both HSV-1 and HSV-2. The results are shown in Table 4.

TABLE 4

| Glycerin Extract | Dilution | Results | |
|---|---|---|---|
| | | HSV-1 | HSV-2 |
| Aloe | $10^{-3}$ | 100* | 100 |
| Frangula | $10^{-3}$ | 100 | 100 |
| Rhubarb | $10^{-5}$ | 100 | 100 |
| Cascara | $10^{-3}$ | 100 | 100 |
| Senna | $10^{-3}$ | 100 | 100 |
| 50% Glycerol controls | — | 0 | 0 |

*% activity (PRA assay)

EXAMPLE 12

The active compound responsible for the anti-herpes activity has the structural elements of the most common anthraquinones. This was shown by extracting Aloe emodin from Aloin using hot glycerin extraction followed by separation on a radial silica gel TLC plate using toluene plus 10% methanol as the solvent. A sample was tested by the PRA for anti-viral activity ($10^{-2}$ 100%) and the remainder identified as Aloe emodin by Nuclear Magnetic Resonance (N.M.R.). Reduction of this anthraquinone to anthrone resulted in a loss of anti-viral activity.

Hot glycerin extracts from Frangula, Rhubarb, Cascara and Senna were also resolved on radial TLC plates using purified Aloe emodin and a standard marker. The activity from these plants could be separated in a single zone which ran with the purified Aloe emodin marker.

Aloe emodin, or 1,8-dihydroxy-3(hydroxymethyl)anthraquinone, is a known compound occurring in the free state or as a glycoside in several plants. Its structure is given in the Merck index, 10th Edition, monograph 298 (1983).

Except for a few minor bands, the largest single band resolved on these radial TLC plates was identified as an antraquinone or anthraquinone-like compound(s) using the purified aloe emodin marker. Thus the extraction procedures reported here greatly enrich for anthraquinones present in the plants while removing most of the non-active plant products.

EXAMPLE 13

The following are two uncontrolled case studies on human volunteers which demonstrated that a methanol extract (identical to Sample A from Example 5) was effective in treating recurrent Herpes Labialis (cold sores).

A white 47 year old male presented with a 35 year history of sporatic recurrent Herpes Labialis. The lesions have always followed the classic course of tingling prodomal phase with a course of 12-14 days for healing of the vesicles. In two separate recurrences, all clinical manifestations were aborted by treating the tingling prodomal area topically with an aloe leaf extract at the onset of symptoms. No vesicles subsequently developed. A third episode at the vesicle stage was treated topically with the extract and showed complete healing in two days. No adverse side effects were noted.

A white 45 year old male presented with a 20 year history of recurrent Herpes Labialis. Each episode of recurrence began with a course of tingling during the prodomal stage with a course of 7-9 days for healing of the vesicles. In one episode the subject noted a tingling in the lip and a small cluster of vesicles had formed by the next day. Two topical applications of an aloe extract were applied 12 hours apart. The vesicles did not progress further and by day two showed marked healing. By the third day the vesicles were completely healed. No adverse side effects were noted.

DISCUSSION OF RESULTS

We have discovered that there exists in the gel, sap and leaves of the *Aloe vera* plant an anthraquinone that has anti-viral activity against both HSV-1 and HSV-2. This activity can also be demonstrated in other plants rich in anthraquinone-like compounds. These plant sources are by no means exhaustive. Anthraquinones and anthraquinone-like compounds are present in numerous other plants and certain fungi and can be isolated by the skilled technician using procedures similar to the examples described herein. The anti-viral activity has been purified and identified from *Aloe vera* as aloe emodin. Activity from other plant sources resides in a compound that has structural elements of the most common anthraquinones.

The compounds of the present invention are also believed to be active against other viruses as well and such activity may be determined by the skilled technician using procedures similar to the models described here. Although the active compounds tested have a direct virucidal effect on HSV by the PRA method described here, it is unknown if the compounds will have effects on the intracellular replication cycle of HSV and/or other viruses or be effective by systemic administration.

What is claimed is:

1. A method of treating type 1 or type 2 herpes simplex virus comprising the successive steps of:
   (1) topically applying to the virus-affected areas of a person suffering from said virus, a topically effective amount of an anthraquinone-containing plant extract, said extract obtained from the group consisting of the gel, sap or leaves of *Aloe vera*, the bark of *Rhamnus frangula*, the bark of *Phramnus purshiana*, the leaves of *Cassia angustifolia*, and the rhizomes of *Rheum rhaponticum*; and
   (2) repeating said topical application as required until the desired anti-viral effect is observed.

2. The method of claim 1 wherein the anthraquinone-containing extract is an extract containing *Aloe emodin*.

3. The method of claim 2 wherein the anthraquinone-containing extract is a methanol, ethanol, ethyl acetate, acetone, or glycerin extract of the *Aloe vera* plant.

4. A method of inhibiting the transmission of type 1 or type 2 herpes simplex virus comprising
   applying to the body part of a person capable of being exposed to said virus, a topically effective amount of an anthraquinone-containing plant extract, said extract obtained from the group consisting of the gel, sap or leaves of *Aloe vera,* the bark of *Rhamnus frangula,* the bark of *Rhamnus purshiana,* the leaves of *Cassia angustifolia,* and the rhizomes of *Rheum rhaponticum.*

5. The method of claim 4 in which the anthraquinone-containing extract is an extract containing *Aloe emodin.*

6. A method of treating type 1 or type 2 herpes simplex virus comprising the successive steps of:
 (1) topically applying to the virus-affected areas of a person suffering from said virus, a topically effective amount of an anthraquinone-containing plant extract having an antiviral effect on type 1 or type 2 herpes simplex virus, and
 (2) repeating said topical application as required until the desired anti-viral effect is observed.

7. The method of claim 6 wherein the anthraquinone-containing extract is an extract containing *Aloe emodin.*

8. The method of claim 6 wherein the anthraquinone-containing extract is a methanol, ethanol, ethyl acetate, acetone, or glycerin extract of the *Aloe vera* plant.

* * * * *